United States Patent
Muller et al.

(10) Patent No.: US 6,762,195 B2
(45) Date of Patent: Jul. 13, 2004

(54) PHARMACEUTICALLY ACTIVE ISOINDOLINE DERIVATIVES

(75) Inventors: George Muller, Bridgewater, NJ (US); Hon-Wah Man, Neshanic Station, NJ (US); David I. Stirling, Somerville, NJ (US)

(73) Assignee: Celgene Corporation, Warren, NJ (US)

( * ) Notice: Subject to any disclaimer, the term of this patent is extended or adjusted under 35 U.S.C. 154(b) by 0 days.

(21) Appl. No.: 10/262,210

(22) Filed: Sep. 30, 2002

(65) Prior Publication Data

US 2003/0069428 A1 Apr. 10, 2003

Related U.S. Application Data

(63) Continuation of application No. 09/712,550, filed on Nov. 14, 2000, now Pat. No. 6,458,810.

(51) Int. Cl.[7] .................. A61K 31/445; A61K 31/47; C07D 401/00

(52) U.S. Cl. ................. 514/319; 514/323; 546/201
(58) Field of Search .................. 546/201; 514/319, 514/323

(56) References Cited

U.S. PATENT DOCUMENTS 6,458,810 B1 * 10/2002 Muller et al. ............... 514/323

* cited by examiner

Primary Examiner—Alan L. Rotman
Assistant Examiner—Raymond Covington
(74) Attorney, Agent, or Firm—Pennie & Edmonds LLP

(57) ABSTRACT

Isoindolin-1-one and Isoindoline-1,3-dione substituted in the 2-position with a 2,6-dioxo-3-hydroxypiperidin-5-yl group, which may be further substituted in the 5-position with alkyl or halogeno, and in the 4-position with alkyl or a nitrogen-containing group are inhibitors of, and thus useful in the treatment of disease states mediated by, TNFα. A typical embodiment is 2-(2,6-dioxo-3-hydroxy-5-fluoro-piperidin-5-yl)-4-aminoisoindolin-1-one.

22 Claims, No Drawings

PHARMACEUTICALLY ACTIVE ISOINDOLINE DERIVATIVES

This is a Continuation of application Ser. No. 09/712,550 filed Nov. 14, 2000 now U.S. Pat. No. 6,458,810.

The present invention pertains to non-polypeptide isoindoline derivatives that decrease the levels of tumor necrosis factor alpha (TNFα) and to the treatment of disease states mediated thereby. The compounds inhibit angiogenesis and are useful in the treatment of cancer, inflammatory, and autoimmune diseases. For example, compounds that selectively inhibit TNFα are useful in treating inflammation and effecting relaxation of airway smooth muscle with a minimum of unwanted side effects, e.g., cardiovascular or antiplatelet effects. The present invention also relates to methods of treatment and pharmaceutical compositions utilizing such compounds.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., Nature 330, 662–664 (1987) and Hinshaw et al., Circ. Shock 30, 279–292 (1990)}; rheumatoid arthritis, Crohn's disease, IBD, cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712–714 (1989)}. Systemic infusion of recombinant TNFα also resulted in changes typically seen in ARDS {Ferrai-Baliviera et al, Arch. Surg. 124(12),1400–1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516–518 (1986) and Johnson et al., Endocrinology 124(3), 1424–1427 (1989)}. TNFα also has been shown to stimulate bone resorption and inhibit bone formation in vitro and in vivo through stimulation of osteoblast formation and activation combined with inhibition of osteoblast function. Although TNFα may be involved in many bone resorption diseases, including arthritis, a most compelling link with disease is the association between production of TNFα by tumor or host tissues and malignancy associated hypercalcemia {Calci. Tissue Int. (US) 46(Suppl.), S3–10 (1990)}. In Graft versus Host Reaction, increased serum TNFα levels have been associated with major complication following acute allogenic bone marrow transplants {Holler et al., Blood, 75(4), 1011–1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320(24), 1586–1591 (1989)}.

Unregulated angiogenesis is pathologic and sustains progression of many neo-plastic and non-neoplastic diseases including solid tumor growth and metastases, arthritis, some types of eye disorders, and psoriasis. See, e.g., Moses et al., 1991, Biotech. 9:630–634; Folkman et al., 1995, N. Engl. J. Med., 333:1757–1763; Auerbach et al., 1985, J. Microvasc. Res. 29:401–411; Folkman, 1985, Advances in Cancer Research, eds. Klein and Weinhouse, Academic Press, New York, pp. 175–203; Patz, 1982, Am. J. Opthalmol. 94:715–743; Folkman et al., 1983, Science 221:719–725; and Folkman and Kiagsbrun, 1987, Science 235:442–447. In addition, maintenance of the avascularity of the cornea, lens, and trabecular meshwork is crucial for vision as well as to ocular physiology. See, e.g., reviews by Waltman et al., 1978, Am. J. Ophthal. 85:704–710 and Gartner et al., 1978, Surv. Ophthal. 22:291–312.

Angiogenesis thus is encountered in various disease states, tumor metastasis, and abnormal growth by endothelial cells. Pathological states created by unregulated angiogenesis have been grouped together as angiogenic dependent or angiogenic associated diseases. Control of the angiogenic processes could lead to the mitigation of these conditions.

The components of angiogenesis relating to vascular endothelial cell proliferation, migration and invasion, have been found to be regulated in part by polypeptide growth factors. Endothelial cells exposed to a medium containing suitable growth factors can be induced to evoke some or all of the angiogenic responses. Polypeptides with in vitro endothelial growth promoting activity include acidic and basic fibroblast growth factors, transforming growth factors α and β, platelet-derived endothelial cell growth factor, granulocyte colony-stimulating factor, interleukin-8, hepatocyte growth factor, proliferin, vascular endothelial growth factor and placental growth factor. Folkman et al., 1995, N. Engl. J. Med., 333:1757–1763.

Inhibitory influences predominate in the naturally occurring balance between endogenous stimulators and inhibitors of angiogenesis. Rastinejad et al., 1989, Cell 56:345–355. In those instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Macrophage-induced angiogenesis is known to be mediated by TNFα. Leibovich et al. {Nature, 329, 630–632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth.

TNFα production also has been independently associated with cancerous conditions, particularly induced tumors {Ching et al., Brit. J. Cancer, (1955) 72, 339–343, and Koch, Progress in Medicinal Chemistry, 22, 166–242 (1985)}. Whether or not involved with TNFα production, angiogenesis is prominent in solid tumor formation and metastasis and angiogenic factors have been found associated with several solid tumors such as rhabdomyosarcomas, retinoblastoma, Ewing sarcoma, neuroblastoma, and osteosarcoma. Tumors in which angiogenesis is important include solid tumors, and benign tumors such as acoustic neuroma, neurofibroma, trachoma and pyogenic granulomas. Independent of its action on TNFα production, the prevention of angiogenesis could halt the growth of these tumors and the resultant damage to the animal due to the presence of the tumor. Angiogenesis has been associated with blood-born tumors such as leukemias and various acute or chronic neoplastic diseases of the bone marrow. In such conditions, unrestrained proliferation of white blood cells occurs, usually accompanied by anemia, impaired blood clotting, and enlargement of the lymph nodes, liver, and spleen.

Angiogenesis also is involved in tumor metastasis. Thus angiogenesis stimulation occurs in vascularization of the tumor, allowing tumor cells to enter the blood stream and circulate throughout the body. After the tumor cells have left the primary site, and have settled into the secondary, metastasis site, angiogenesis must occur before the new tumor can grow and expand.

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245–247 (1990)}. High levels of TNFα production (in the serum and in isolated macrophages) have been demonstrated in animal models of silica and asbestos induced fibrosis {Bissonnette et al., Inflammation 13(3), 329–339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 3642 (1990)}.

TNFα is also implicated in the inflammatory response which follows reperfusion, called reperfusion injury, and is a major cause of tissue damage after loss of blood flow {Vedder et al., PNAS 87, 2643–2646 (1990)}. TNFα also alters the properties of endothelial cells and has various pro-coagulant activities, such as producing an increase in tissue factor pro-coagulant activity and suppression of the anticoagulant protein C pathway as well as down-regulating the expression of thrombomodulin {Sherry et al., J. Cell Biol. 107, 1269–1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J Path. 135(1), 121–132 (1989)}.

TNFα blockage with monoclonal anti-TNFα antibodies has been shown to be beneficial in rheumatoid arthritis {Elliot et al., Int. J. Pharmac. 1995 17(2), 141–145} and Crohn's disease {von Dullemen et al., Gastroenterology, 1995 109(1), 129–135}

Moreover, it now is known that TNFα is a potent activator of retrovirus replication including activation of HIV-1. {Duh et al., Proc. Nat. Acad. Sci. 86, 5974–5978 (1989); Poll et al., Proc. Nat Acad. Sci. 87, 782–785 (1990); Monto et al., Blood 79, 2670 (1990); Clouse et al., J. Immunol. 142, 431–438 (1989); Poll et al., AIDS Res. Hum. Retrovirus, 191–197 (1992)}. AIDS results from the infection of T lymphocytes with Human Immunodeficiency Virus (HIV). At least three types or strains of HIV have been identified; i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al., Proc. Natl. Acad. Sci., 87, 782–784 (1990)}; therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osbom, et al., PNAS 86 2336–2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., PNAS 86, 2365–2368 (1989)}. A molecular mechanism for the virus inducing activity is suggested by TNFα' ability to activate a gene regulatory protein (NFκB) found in the cytoplasm of cells, which promotes HIV replication through binding to a viral regulatory gene sequence (LTR) {Osborn et al., PNAS 86, 2336–2340 (1989)}. TNFα in AIDS associated cachexia is suggested by elevated serum TNFα and high levels of spontaneous TNFα production in peripheral blood monocytes from patients {Wright et al., J. Immunol. 141(1), 99–104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., Cell 1989, 58, 227–29). NFκB has been implicated as a transcriptional activator in a variety of disease and inflammatory states and is thought to regulate cytokine levels including but not limited to TNFα and also to be an activator of HIV transcription (Dbaibo, et al., J Biol. Chem. 1993, 17762–66; Duh et al., Proc. Natl. Acad. Sci. 1989, 86, 5974–78; Bachelerie et al., Nature 1991, 350, 709–12; Boswas et al., J Acquired Immune Deficiency Syndrome 1993, 6, 778–786; Suzuki et al., Biochem. And Biophys. Res. Comm. 1993, 193, 277–83; Suzuki et al., Biochem. And Biophys. Res. Comm. 1992, 189, 1709–15; Suzuki et al., Biochem. Mol. Bio. Int. 1993, 31(4), 693–700; Shakhov et al., Proc. Natl. Acad. Sci. USA 1990, 171, 35–47; and Staal et al., *Proc. Natl. Acad. Sci. USA* 1990, 87, 994347). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, cancer, septic shock, sepsis, endotoxic shock, graft versus host disease, wasting, Crohn's disease, inflammatory bowel disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Decreasing TNFα levels thus constitute valuable therapeutic strategies for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury.

DETAILED DESCRIPTION

The present invention pertains to compounds of Formula I in which the carbon atoms designated * constitute centers of chirality:

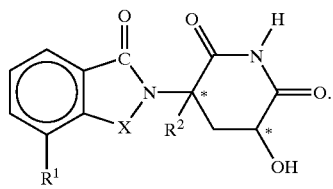

In Formula I,
X is —C(O)— or —CH$_2$—;
R$^1$ is alkyl of 1 to 8 carbon atoms or —NHR$^3$;
R$^2$ is hydrogen, alkyl of 1 to 8 carbon atoms, or halogeno; and
R$^3$ is
  hydrogen,
  alkyl of 1 to 8 carbon atoms,
  cycloalkyl of 3 to 18 carbon atoms,
  phenyl, unsubstituted or substituted with halo, amino, or alkylamino of 1 to 4 carbon atoms,
  benzyl, unsubstituted or substituted with halo, amino, or alkylamino of 1 to 4 carbon atoms, or
  —COR$^4$ in which
    R$^4$ is
      hydrogen,
      alkyl of 1 to 8 carbon atoms, unsubstituted or substituted with halo, amino, or alkylamino of 1 to 4 carbon atoms,
      cycloalkyl of 3 to 18 carbon atoms,
      phenyl, unsubstituted or substituted with halo, amino, or alkylamino of 1 to 4 carbon atoms, or
      benzyl, unsubstituted or substituted with halo, amino, or alkylamino of 1 to 4 carbon atoms.

The present invention also pertains to the acid addition salts of these isoindoline derivatives which are susceptible of protonation. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The compounds can be prepared through a number of methods. For example, a suitably protected 3,5-disubstituted piperidine-2,6-dione of Formula II is allowed to react with a 4-substituted 1,3-dihydroisobenzofuran-1,3-dione of Formula III to yield the protected compounds of Formula IA:

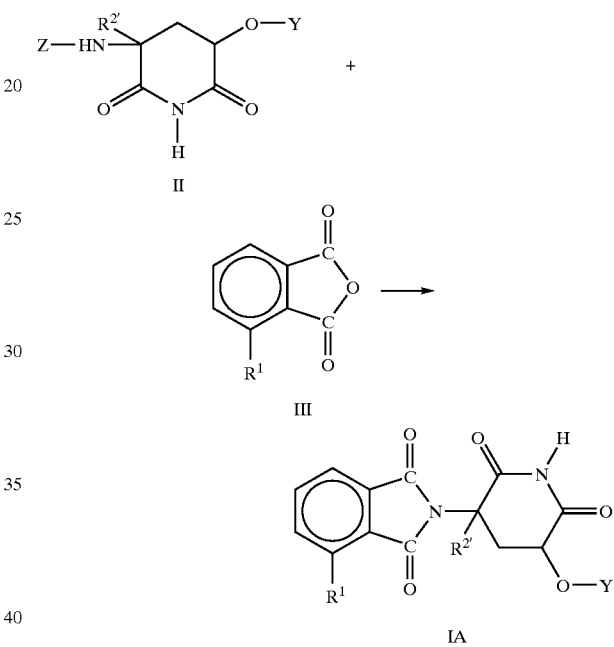

In the foregoing reaction, R$^1$ is as defined above, X is —CH$_2$—, R$^{2'}$ is hydrogen or alkyl, and Z and Y are protecting groups, as for example benzyloxycarbonyl and alkanoyloxy.

When X is —CH$_2$—, a piperidine-2,6-dione of Formula II is allowed to react with disubstituted alkyl benzoate of Formula IIIA:

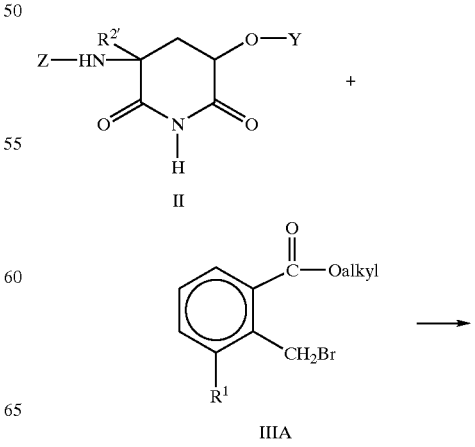

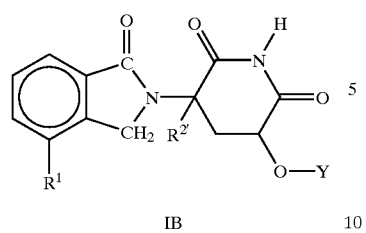

IB

Compounds of Formulas III and IIIA are known. Compounds of Formula II in which $R^{2'}$ is hydrogen can be prepared by treating an amino protected lactone of 2-amino-4-hydroxyglutaric acid of Formula IIA with ammonia in methanol to yield the corresponding protected 2-amino-4-hydroxy-4-carboxybutanamide of Formula IIB which is then subjected to cyclization in acetic acid:

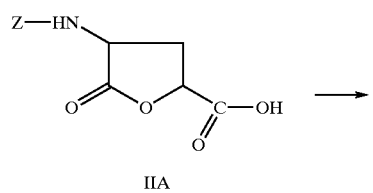

IIA

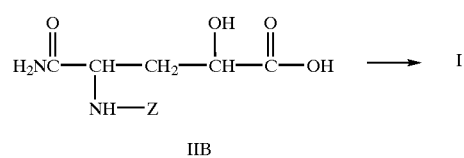

IIB

When $R^{2'}$ is alkyl, it can be introduced by treating the lactone of Formula IIA with two equivalents of a strong base, as for example n-butyl lithium, to form the dianion, and then alkylating, as for example with methyl iodide. Alternatively, the unprotected lactone IIC is converted to the t.-butyl ester which in turn is treated with benzaldehyde to form the amidine IID. Treatment of the amidine with base and an alkyl halide results in alkylation of the α-carbon atom in compound IIE and subsequent treatment with acid cleaves both the t.-butyl ester and amidine yielding the intermediate IIF which can then be reprotected as the benzyloxycarbonyl derivative.

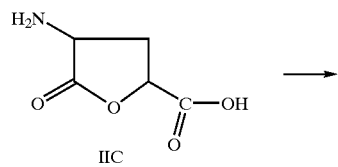

IIC

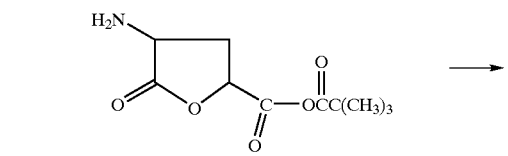

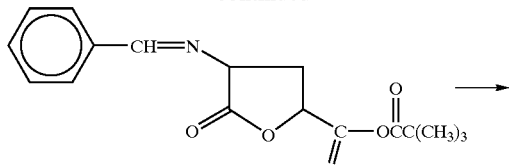

IID

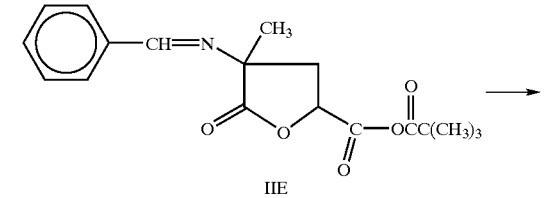

IIE

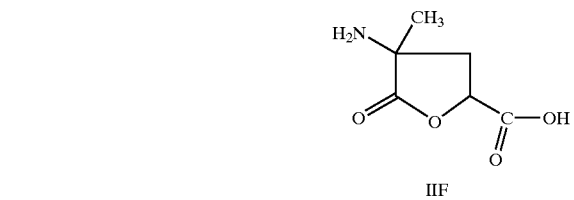

IIF

When $R^2$ is halogeno, as for example fluoro, it can be introduced by treating a compound of Formula IA or IB with sodium bis(trimethylsilyl)amide and N-fluorobenzenesulfonimide:

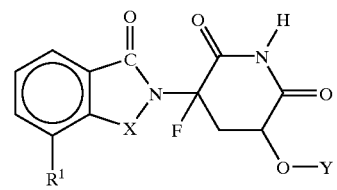

IC

Removal of the protecting group Y can be achieved through appropriate hydrolysis; e.g., treatment with p-toluenesulfonic acid to cleave an alkanoyloxy group.

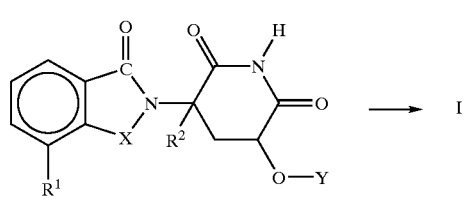

IA, IB, IC

As is apparent from the foregoing, it often is advantageous to utilized protected groups including but not limited to functional groups convertible to the desired group. Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed or converted to the desired group at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol.15/I, Georg Thieme Verlag, Stuttgart 1974, the disclosures of which are incorporated herein by reference.

An amino group thus can be protected as an amide utilizing an acyl group which is selectively removable under mild conditions, especially formyl, a lower alkanoyl group which is branched in 1- or α position to the carbonyl group, particularly tertiary alkanoyl such as pivaloyl, or a lower alkanoyl group which is substituted in the position α to the carbonyl group, as for example trifluoroacetyl.

Should a carboxy group require protection, it can be converted to an ester which is selectively removable under sufficiently mild conditions not to disrupt the desired structure of the molecule, especially a lower alkyl ester of 1 to 12 carbon atoms such as methyl or ethyl and particularly one which is branched at the 1- or α position such as t-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichloroethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as trimethylsilylethyl or tri-lower alkylsilyl, as for example trimethylsilyloxycarbonyl.

When $R^1$ is amino, the reactions described herein can be performed with intermediates in which $R^1$ is a nitro group with the nitro group then being catalytically reduced (hydrogenated) to an amine. Similarly when $R^1$ is derivative of an amino group, such as N-acylamino or N-alkylamino it can be formed from the corresponding unsubstituted amino compound.

The compounds contain two centers of chirality (designated by * in Formula I) and thus can exist as enantiomers and diastereoisomers. The compounds can be administered as a substantially chirally pure (S,S)-, (S,R)-, (R,R)-, or (R,S)-isomer or as mixtures of two or more of these isomers and all are within the scope of the present invention. Mixtures can be used as such or can be separated into their individual isomers mechanically as by chromatography using a chiral absorbent. Alternatively, the individual isomers can be prepared in chiral form or separated chemically from a mixture by forming salts with a chiral acid, or have such as the individual enantiomers of 10-camphorsulfonic acid, camphoric acid, bromocamphoric acid, methoxyacetic acid, tartaric acid, diacetyltarta acid, malic acid, pyrrolidone-5-carboxylic acid, and the like, and then freeing one or both of the resolved bases, optionally repeating the process, so as obtain either or both substantially free of the other; ie., in a form having an optical purity of >95%.

A first preferred subgroup are those compounds of Formula I in which $R^2$ is hydrogen, methyl, or fluoro, particularly hydrogen.

A second preferred subgroup are those compounds of Formula I in which $R^1$ is amino.

A third preferred subgroup are those compounds of Formula I in which $R^1$ is methyl.

A fourth preferred subgroup are those compounds of Formula I in which X is —C(O)—.

A fifth preferred subgroup are those compounds of Formula I in which X is —CH$_2$—

A further preferred subgroup are those compounds of Formula I in which $R^2$ is hydrogen, methyl, or fluoro, particularly hydrogen, $R^1$ is methyl, amino, alkylamino, or acylamino, and X is —C(O)— or —CH$_2$—.

Inhibition of TNFα and NFκB by these compounds can be conveniently assayed using methods known in the art, e.g., enzyme immunoassay, radioimmunoassay, immunoelectrophoresis, affinity labeling, etc., of which the following are typical.

Representative compounds include 2-(2,6-dioxo-3-hydroxy-5-fluoropiperidin-5-yl)-4-(N-benzylamino) isoindoline-1,3-dione; 2-(2,6-dioxo-3-hydroxy-5-fluoropiperidin-5-yl)-4-(N-benzylamino)isoindolin-1-one; 2-(2,6-dioxo-3-hydroxy-5-fluoropiperidin-5-yl)-4-acetamidoisoindoline-1,3-dione; 2-(2,6-dioxo-3-hydroxy-5-fluoropiperidin-5-yl)-4-acetamidoisoindolin-1-one; 2-(2,6-dioxo-3-hydroxy-5-fluoropiperidin-5-yl)-4-aminoisoindolin-1-one; 2-(2,6-dioxo-3-hydroxy-5-fluoropiperidin-5-yl)-4-aminoisoindoline-1,3-dione; 2-(2,6-dioxo-3-hydroxy-5-fluoropiperidin-5-yl)-4-methylaminoisoindoline-1,3-dione; 2-(2,6-dioxo-3-hydroxy-5-fluoropiperidin-5-yl)-4-methylaminoisoindolin-1-one; 2-(2,6-dioxo-3-hydroxy-5-fluoropiperidin-5-yl)-4-methylisoindoline-1,3-dione; 2-(2,6-dioxo-3-hydroxy-5-fluoropiperidin-5-yl)-4-methylisoindolin-1-one; 2-(2,6-dioxo-3-hydroxy-5-methylpiperidin-5-yl)-4-(N-benzylamino)isoindoline-1,3-dione; 2-(2,6-dioxo-3-hydroxy-5-methylpiperidin-5-y)-4-(N-benzylamino)isoindolin-1-one; 2-(2,6-dioxo-3-hydroxy-5-methylpiperidin-5-yl)-4-acetamidoisoindoline-1,3-dione; 2-(2,6-dioxo-3-hydroxy-5-methylpiperidin-5-yl)-4-acetamidoisoindolin-1-one; 2-(2,6-dioxo-3-hydroxy-5-methylpiperidin-5-yl)-4-aminoisoindolin-1-one; 2-(2,6-dioxo-3-hydroxy-5-methylpiperidin-5-yl)-4-aminoisoindoline-1,3-dione; 2-(2,6-dioxo-3-hydroxy-5-methylpiperidin-5-yl)-4-methylaminoisoindoline-1,3-dione; 2-(2,6-dioxo-3-hydroxy-5-methylpiperidin-5-yl)-4-methylaminoisoindolin-1-one; 2-(2,6-dioxo-3-hydroxy-5-methylpiperidin-5-yl)-4-methylisoindoline-1,3-dione; 2-(2,6-dioxo-3-hydroxy-5-methylpiperidin-5-yl)-4-methylisoindolin-1-one; 2-(2,6-dioxo-3-hydroxypiperidin-5-yl)-4-(N-benzylamino)isoindoline-1,3-dione; 2-(2,6-dioxo-3-hydroxypiperidin-5-yl)-4-(N-benzylamino)isoindolin-1-one; 2-(2,6-dioxo-3-hydroxypiperidin-5-yl)-4-acetamidoisoindolin-1-one; 2-(2,6-dioxo-3-hydroxypiperidin-5-yl)-4-acetamidoisoindoline-1,3-dione; 2-(2,6-dioxo-3-hydroxypiperidin-5-yl)-4-aminoisoindolin-1-one; 2-(2,6-dioxo-3-hydroxypiperidin-5-yl)-4-aminoisoindoline-1,3-dione; 2-(2,6-dioxo-3-hydroxypiperidin-5-yl)-4-methylaminoisoindolin-1-one; 2-(2,6-dioxo-3-hydroxypiperidin-5-yl)-4-methylaminoisoindoline-1,3-dione; 2-(2,6-dioxo-3-hydroxypiperidin-5-yl)-4-methylisoindolin-1-one; and 2-(2,6-dioxo-3-hydroxypiperidin-5-yl)-4-methylisoindoline-1,3-dione.

PBMC from normal donors are obtained by Ficoll-Hypaque density centrifugation. Cells are cultured in RPMI supplemented with 10% AB+ serum, 2 mM L-glutamine, 100 U/mL penicillin and 100 mg/mL streptomycin.

The test compounds are dissolved in dimethylsulfoxide (Sigma Chemical), further dilutions are done in supplemented RPMI. The final dimethylsulfoxide concentration in the presence or absence of drug in the PBMC suspensions is 0.25 wt %. The test compounds are assayed at half-log dilutions starting at 50 mg/mL. The test compounds are added to PBMC ($10^6$ cells/mL) in 96 wells plates one hour before the addition of LPS.

PBMC ($10^6$ cells/mL) in the presence or absence of test compound are stimulated by treatment with 1 mg/mL of LPS from *Salmonella minnesota* R595 (List Biological Labs, Campbell, Calif.). Cells are then incubated at 37° C. for 18–20 hours. Supernatants areharvested and assayed immediately for TNFα levels or kept frozen at −70° C. (for not more than 4 days) until assayed.

The concentration of TNFα in the supernatant is determined by human TNFα ELISA kits (ENDOGEN, Boston, Mass.) according to the manufacturer's directions.

The compounds can be used, under the supervision of qualified professionals, to inhibit the undesirable effects of TNFα and NFκB. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20–100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 1000 milligrams/day as needed in single or multiple daily administration. In general, an initial treatment regimen can be copied from that known to be effective in interfering with TNFα activity for other TNFα mediated disease states by the compounds of the present invention. Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is observed following the normal treatment regimen, then the amount of cytokine activity interfering agent administered is increased, e.g., by fifty percent a week.

The compounds of the present invention can also be used topically in the treatment or prophylaxis of topical disease states mediated or exacerbated by excessive TNFα production, such as viral infections, for example those caused by the herpes viruses or viral conjunctivitis, psoriasis, other skin disorders and diseases, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The invention thus includes various methods of treatment including the method of reducing or inhibiting undesirable levels of TNFα, method of reducing or inhibiting undesirable levels of matrix metalloproteinases, the method of treating undesirable angiogenesis, the method of treating cancer, the method of treating inflammatory disease, the method of treating autoimmune disease, the method of treating arthritis, the method of treating rheumatoid arthritis, the method of treating inflammatory bowel disease, the method of treating Crohn's disease, the method of treating aphthous ulcers, the method of treating cachexia, the method of treating graft versus host disease, the method of treating asthma, the method of treating adult respiratory distress syndrome, and the method of treating acquired immune deficiency syndrome, by administering to a mammalan an effective amount of a substantially chirally pure (R)- or (S)-isomer of a compound of Formula I or a mixture of those isomers. While these methods may overlap, they also may differ in terms of method of administration, dose level, dosage regimen (such as single or multiple doses), and concurrently administered therapeutic agents.

The invention also includes pharmaceutical compositions in which (i) a quantity of a substantially chirally pure (R)- or (S)-isomer of a compound of Formula I or a mixture of those isomers, that upon administration in a single or multiple dose regimen is pharmaceutically effective is combined with (ii) a pharmaceutically acceptable carrier.

Pharmaceutical compositions can be typified by oral dosage forms that include tablets, capsules, dragees, and similar shaped, compressed pharmaceutical forms containing from 1 to 100 mg of drug per unit dosage. Mixtures containing from 20 to 100 mg/mL can be formulated for parenteral administration which includes intramuscular, intrathecal, intravenous and intra-arterial routes of administration. Rectal administration can be effected through the use of suppositories formulated from conventional carriers such as cocoa butter.

Pharmaceutical compositions will comprise one or more compounds of the pres??ent invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone polyvinylpyrrolidone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

The following examples will serve to further typify the nature of this invention but should not be construed as a limitation in the scope thereof, which scope is defined solely by the appended claims.

EXAMPLE 1

2-(5-Hydroxy-2,6-dioxopiperid-3-yl))-4-methylisoindoline-1,3-dione

A. 3-(4-Methyl-1,3-dioxoisoindolin-2-yl)-2,6-dioxo-5-acetoxypiperidine

A mixture of 2,6-dioxo-3-benzyloxycarbonylamino-5-acetoxypiperidine (9 g, 28.2 mmol) (U. Teubert et al, *Arch. Pharm. Pharm. Med. Chem.* (1998) 7–12) and Pd/C (10%, 0.9 g) in acetic acid (90 mL) is shaken under hydrogen (50–60 psi) for 3 hours. The suspension is filtered through a pad of Celite and washed with acetic acid. To the filtrate is added 3-methylphthalic anhydride (4.56 g, 28.2 mmol) and this mixture is heated at reflux for 18 hours. The solvent is removed in vacuo to give 3-(4-methyl-1,3-dioxoisoindolin-2-yl)-2,6-dioxo-5-acetoxypiperidine which can be further purified by column chromatography.

B. 2-(5-Hydroxy-2,6-dioxopiperid-3-yl)-4-methylisoindoline-1,3-dione

A solution of 3-(4-methyl-1,3-dioxoisoindolin-2-yl)-2,6-dioxo-5-acetoxypiperidine (1 g, 3.5 mmol) and p-toluenesulfonic acid (0.33 g, 1.8 mmol) in methanol (10 mL) is heated at reflux for 5 hours. The solvent is removed in vacuo to give 2-(5-hydroxy-2,6-dioxopiperid-3-yl)-4-methylisoindoline-1,3-dione. The product can be further purified by column chromatography.

EXAMPLE 2

4-Amino-2-(5-hydroxy-2,6-dioxopiperid-3-yl)isoindoline-1,3-dione

A. 5-(4-Nitro-1,3-dioxoisoindolin-2-yl)-2,6-dioxo-5-acetoxypiperidine

A solution of 2,6-dioxo-3-benzyloxycarbonylamino-5-acetoxypiperidine (9 g, 28.2 mmol) and Pd/C (10%, 0.9 g) in acetic acid (90 mL) is shaken under hydrogen (50–60 psi) for 3 hours. The suspension is filtered through a pad of Celite and washed with acetic acid. To the filtrate is added 3-nitrophthalic anhydride (5.4 g, 28.2 mmol), this mixture is heated at reflux for 18 hours, and the solvent is then removed in vacuo to give 3-(4-nitro-1,3-dioxoisoindolin-2-yl)-2,6-dioxo-5-acetoxypiperidine which can be further purified by column chromatography.

B. 3-(4-Amino-1,3-dioxoisoindolin-2-yl)-2,6-dioxo-5-acetoxypiperidine

A solution of 3-(4-nitro-1,3-dioxoisoindolin-2-yl)-2,6-dioxo-5-acetoxypiperidine (1 g, 3.1 mmol) and Pd/C (10%, 0.1 g) in methanol (100 mL) is shaken under hydrogen (50–60 psi) for 3 hours. The suspension is filtered through a pad of Celite and washed with methanol to give 3-(4-amino-1,3-dioxoisoindolin-2-yl)-2,6-dioxo-5-acetoxypiperidine which can be further purified by column chromatography.

C. 4-Amino-2-(5-hydroxy-2,6-dioxopiperid-3-yl)isoindoline-1,3-dione

A solution of 3-(4-amino-1,3-dioxoisoindolin-2-yl)-2,6-dioxo-5-acetoxypiperidine (1 g, 3.5 mmol) and p-toluenesulfonic acid (0.33 g, 1.8 mmol) in methanol (10 mL) is heated at reflux for 5 hours. The solvent is then removed in vacuo to give 4-amino-2-(5-hydroxy-2,6-dioxopiperid-3-yl)isoindoline-1,3-dione which can be further purified by column chromatography.

EXAMPLE 3

4-Nitro-2-(5-hydroxy-2,6-dioxopiperid-3-yl)isoindoline-1-one

A. 3-(4-Nitro-1-oxoisoindolin-2-yl)-2,6-dioxo-5-acetoxypiperidine

A solution of 2,6-dioxo-3-benzyloxycarbonylamino-5-acetoxypiperidine (9 g, 28.2 mmol) and Pd/C (10%, 0.9 g) in acetic acid (90 mL) is shaken under hydrogen (50–60 psi) for 3 hours. The suspension is filtered through a pad of Celite and washed with acetic acid and the solvent is then removed in vacuo. The residue, triethylamine (2.9 g, 28 mmol), and methyl 2-bromomethyl-3-nitrobenzoate (7.7 g, 28.2 mmol) in dimethylformamide (100 mL) is heated at 80° C. for 18 hours. The solvent is removed in vacuo to give 3-(4-nitro-1-oxoisoindolin-2-yl)-2,6-dioxo-5-acetoxy-piperidine which can be further purified by column chromatography.

B. 4-Nitro-2-(5-hydroxy-2,6-dioxopiperid-3-yl)isoindoline-1-one

A solution of 3-(4-nitro-1-oxoisoindolin-2-yl)-2,6-dioxo-5-acetoxypiperidine (0.96 g, 3.5 mmol) and p-toluenesulfonic acid (0.33 g, 1.8 mmol) in methanol (10 mL) is heated at reflux for 5 hours. The solvent is removed in vacuo to give 4-nitro-2-(5-hydroxy-2,6-dioxopiperid-3-yl)isoindoline-1-one which is further purified by column chromatography.

EXAMPLE 4

4-Amino-2-(5-hydroxy-2,6-dioxopiperid-3-yl)isoindoline-1-one

A. 3-(4-Amino-1-oxoisoindolin-2-yl)-2,6-dioxo-5-acetoxypiperidine

A solution of 3-(4-nitro-1-oxoisoindolin-2-yl)-2,6-dioxo-5-acetoxypiperidine (0.9 g, 3.1 mmol) and Pd/C (10%, 0.1 g) in methanol (100 mL) is shaken under hydrogen (50–60 psi) for 3 hours. The suspension is filtered through a pad of Celite and washed with methanol to give 3-(4-amino-1-oxoisoindolin-2-yl)-2,6-dioxo-5-acetoxypiperidine which is further purified by column chromatography.

B. 4-Amino-2-(5-hydroxy-2,6-dioxopiperid-3-yl)isoindoline-1-one

A solution of 3-(4-amino-1-oxoisoindolin-2-yl)-2,6-dioxo-5-acetoxypiperidine (0.96 g, 3.5 mmol) and p-toluenesulfonic acid (0.33 g, 1.8 mmol) in methanol (10 mL) is heated at reflux for 5 hours. The solvent is removed in vacuo to give 4-amino-2-(5-hydroxy-2,6-dioxopiperid-3-yl)isoindoline-1-one which is further purified by column chromatography.

EXAMPLE 5

3-[1,3-Dioxo-4-benzamidoisoindolin-2-yl]-2,6-dioxo-5-hydroxypiperidine

A. 3-[1,3-Dioxo-4-benzamidoisoindolin-2-yl]-2,6-dioxo-5-acetoxypiperidine

A stirred solution of 3-(4-amino-1,3-dioxoisoindolin-2-yl)-2,6-dioxo-5-acetoxypiperidine (1 g, 3.5 mmol) and benzoyl chloride (0.5 g, 3.5 mmol) in tetrahydrofuran (15 mL) is heated at reflux for 1 hour. The solvent is removed in vacuo to give 3-[1,3-dioxo-4-benzoyllaminoisoindolin-2-yl]-2,6-dioxo-5-acetoxypiperidine which is further purified by column chromatography.

B. 3-[1,3-Dioxo-4-benzamidoisoindolin-2-yl]-2,6-dioxo-5-hydroxypiperidine

A solution of 3-[1,3-dioxo-4-benzamidoisoindolin-2-yl]-2,6-dioxo-5-acetoxypiperidine (1.36 g, 3.5 mmol) and p-toluenesulfonic acid (0.33 g, 1.8 mmol) in methanol (20 mL) is heated at reflux for 5 hours. The solvent is removed in vacuo to give 3-[1,3-dioxo-4-benzamidoisoindolin-2-yl]-2,6-dioxo-5-hydroxypiperidine which is further purified by column chromatography.

EXAMPLE 6
3-[4-(2-Furylcarbonylamino)-1,3-dioxoisoindolin-2-yl]-2,6-dioxo-5-hydroxypiperidine A. 3-[4-(2-Furylcarbonylamino)-1,3-dioxoisoindolin-2-yl]-2,6-dioxo-5-acetoxypiperidine A solution of 3-(4-amino-1,3-dioxoisoindolin-2-yl)-2,6-dioxo-5-acetoxypiperidine (1 g, 3.5 mmol) and 2-furonyl chloride (0.46 g, 3.5 mmol) in tetrahydrofuran (20 mL) is heated at reflux for 1 hour. The solvent is removed in vacuo to give 3-[4-(2-furylcarbonylamino)-1,3-dioxoisoindolin-2-yl]-2,6-dioxo-5-acetoxypiperidine which is further purified by column chromatography.

B. 3-[4-(2-Furylcarbonylamino)-1,3-dioxoisoindolin-2-yl]-2,6-dioxo-5-hydroxypiperidine A solution of 3-[4-(2-furylcarbonylamino)-1,3-dioxoisoindolin-2-yl]-2,6-dioxo-5-acetoxypiperidine (1.33 g, 3.5 mmol) and p-toluenesulfonic acid (0.33 g, 1.8 mmol) in methanol (20 mL) is heated at reflux for 5 hours. The solvent is removed in vacuo to give 3-[4-(2-furylcarbonylamino)-1,3-dioxoisoindolin-2-yl]-2,6-dioxo-5-hydroxypiperidine which is further purified by column chromatography.

EXAMPLE 7
3-[4-Methoxyacetylamino-1,3-dioxoisoindolin-2-yl]-2,6-dioxo-5-hydroxypiperidine A. 3-[4-Methoxyacetylamino-1,3-dioxoisoindolin-2-yl]-2,6-dioxo-5-acetoxypiperidine A solution of 3-(4-amino-1,3-dioxoisoindolin-2-yl)-2,6-dioxo-5-acetoxypiperidine (1 g, 3.5 mmol) and methoxyacetyl chloride (0.38 g, 3.5 mmol) in tetrahydrofuran (20 mL) is heated at reflux for 1 hour. The solvent is removed in vacuo to give 3-[4-(2-methoxyacetylamino)-1,3-dioxoisoindolin-2-yl]-2,6-dioxo-5-acetoxypiperidine which is further purified by column chromatography.

B. 3-[4-Methoxyacetylamino-1,3-dioxoisoindolin-2-yl]-2,6-dioxo-5-hydroxypiperidine A solution of 3-[4-methoxyacetylamino-1,3-dioxoisoindolin-2-yl]-2,6-dioxo-5-acetoxypiperidine (1.26 g, 3.5 mmol) and p-toluenesulfonic acid (0.33 g, 1.8 mmol) in methanol (20 mL) is heated at reflux for 5 hours. The solvent is removed in vacuo to give 3-[4-methoxyacetylamino-1,3-dioxoisoindolin-2-yl]-2,6-dioxo-5-hydroxypiperidine which is further purified by column chromatography.

EXAMPLE 8
3-(4-Fur-2-ylmethylamino-1,3-dioxoisoindolin-2-yl)-5-hydroxypiperidine-2,6-dione A solution of 3-(4-amino-1,3-dioxoisoindolin-2-yl)-5-hydroxypiperidine-2,6-dione (0.82 g, 3.0 mmol) and 2-furaldehyde (0.34 g, 3.5 mmol) in acetic acid (10 mL) is heated at reflux for 4 hours. To the mixture is added sodium borohydride (130 mg, 3.5 mmol) at room temperature and this mixture is maintained for 18 hours. The mixture is worked up to give 3-(4-fur-2-ylmethylamino-1,3-dioxoisoindolin-2-yl)-5-hydroxypiperidine-2,6-dione which is further purified by column chromatography.

EXAMPLE 9
3-(4-Fur-2-ylmethylamino-1-oxoisoindolin-2-yl)-5-hydroxypiperidine-2,6-dione A solution of 3-(4-amino-1-oxoisoindolin-2-yl)-5-hydroxypiperidine-2,6-dione (0.82 g, 3.0 mmol) and 2-furaldehyde (0.34 g, 3.5 mmol) in acetic acid (10 mL) is heated at reflux for 4 hours. To the mixture is added sodium borohydride (130 mg, 3.5 mmol) at room temperature and kept for 18 hours. The mixture is worked up to give 3-(4-fur-2-ylmethylamino-1-oxoisoindolin-2-yl)-5-hydroxypiperidine-2,6-dione which is further purified by column chromatography.

EXAMPLE 10
4-Nitro-2-(3-fluoro-5-hydroxy-2,6-dioxopiperid-3-yl)isoindoline-1,3-dione A. 1-Tert-butoxycarbonyl-3-(4-nitro-1,3-dioxoisoindolin-2-yl)-2,6-dioxo-5-acetoxypiperidine To a stirred suspension of 3-(4-nitro-1,3-dioxoisoindolin-2-yl)-2,6-dioxo-5-acetoxypiperidine (2.5 g, 7.75 mmol) and di-tert-butyl dicarbonate (1.86 g, 8.52 mmol) in 1,4-dioxane (30 mL) is added DMAP (100 mg) at room temperature. The solution is stirred at room temperature for 18 hours. The solvent is removed in vacuo to give 1-tert-butoxycarbonyl-3-(4-nitro-1,3-dioxoisoindolin-2-yl)-2,6-dioxo-5-acetoxypiperidine which is further purified by column chromatography or recrystallization.

A. 3-fluoro-3-(4-nitro-1,3-dioxoisoindolin-2-yl)-2,6-dioxo-5-acetoxypiperidine

To a stirred solution of 1-tert-butoxycarbonyl-3-(4-nitro-1,3-dioxoisoindolin-2-yl)-2,6-dioxo-5-acetoxypiperidine (2.0 g, 4.3 mmol) in tetrahydrofuran (20 mL) is added sodium bis(trimethylsilyl)amide (4.3 mL, 4.3 mmol, 1.0 M) in tetrahydrofuran at −78° C. After 10–30 minutes, N-fluorobenzenesulfonimide (1.1 g, 4.3 mmol) is added to the mixture. The mixture is warmed to room temperature and the solvent is removed in vacuo. The residue is stirred with ethyl acetate (10 mL) and hydrochloric acid (10 mL, 1N) for 1 hour, the organic layer is separated, and the solvent is removed in vacuo to give 3-fluoro-3-(4-nitro-1,3-dioxoisoindolin-2-yl)-2,6-dioxo-5-acetoxypiperidine which is further purified by column chromatography.

B. 4-Nitro-2-(3-fluoro-5-hydroxy-2,6-dioxopiperid-3-yl)isoindoline-1,3-dione

A solution of 3-(4-nitro-1,3-dioxoisoindolin-2-yl)-3-fluoro-2,6-dioxo-5-acetoxypiperidine (1 g, 2.9 mmol) and p-toluenesulfonic acid (0.28 g, 1.5 mmol) in-methanol (10 mL) is heated at reflux for 5 h. The solvent is removed in vacuo to give 4-nitro-2-(3-fluoro-5-hydroxy-2,6-dioxopiperid-3-yl)isoindoline-1,3-dione which is further purified by column chromatography.

EXAMPLE 11
4-Amino-2-(3-fluoro-5-hydroxy-2,6-dioxopiperid-3-yl)isoindoline-1,3-dione A. 3-(4-Amino-1,3-dioxoisoindolin-2-yl)-3-fluoro-2,6-dioxo-5-acetoxypiperidine A solution of 3-fluoro-3-(4-nitro-1,3-dioxoisoindolin-2-yl)-2,6-dioxo-5-acetoxypiperidine (1.0 g, 2.6 mmol) and Pd/C (10%, 0.1 g) in methanol (100 mL) is shaken under hydrogen (50–60 psi) for 3 hours. The suspension is filtered through a pad of Celite and washed with methanol to give 3-(4-amino-1,3-dioxoisoindolin-2-yl)-3-fluoro-2,6-dioxo-5-acetoxypiperidine which is further purified by column chromatography.

B. 4-Amino-2-(3-fluoro-5-hydroxy-2,6-dioxopiperid-3-yl)isoindoline-1,3-dione

A solution of 3-(4-amino-1,3-dioxoisoindolin-2-yl)-3-fluoro-2,6-dioxo-5-acetoxypiperidine (1 g, 2.9 mmol) and p-toluenesulfonic acid (0.28 g, 1.5 mmol) in methanol (10 mL) is heated at reflux for 5 h. The solvent is removed in vacuo to give 4-amino-2-(3-fluoro-5-hydroxy-2,6-dioxopiperid-3-yl)isoindoline-1,3-dione which is further purified by column chromatography.

EXAMPLE 12

Tablets, each containing 50 mg of 2-(2,6-dioxo-3-hydroxypiperidin-5-yl)-4-aminoisoindoline-1,3-dione, can be prepared in the following manner:

| Constituents (for 1000 tablets) | |
| --- | --- |
| 2-(2,6-dioxo-3-hydroxy piperidin-5-yl)-4-amino isoindoline-1,3-dione | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 13

Tablets, each containing 100 mg of 2-(2,6-dioxo-3-hydroxypiperidin-5-yl)-4-methylaminoisoindolin-1-one, can be prepared in the following manner:

| Constituents (for 1000 tablets) | |
| --- | --- |
| 2-(2,6-dioxo-3-hydroxy piperidin-5-yl)-4-methylamino isoindolin-1-one | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

EXAMPLE 14

Tablets for chewing, each containing 75 mg of 2-(2,6-dioxo-3-hydroxy-5-methylpiperidin-5-yl)-4-methylisoindoline-1,3-dione, can be prepared in the following manner:

| Composition (for 1000 tablets) | |
| --- | --- |
| 2-(2,6-dioxo-3-hydroxy-5-methylpiperidin-5-yl)-4-methylisoindoline-1,3-dione | 75.0 g |
| mannitol | 230.0 g |
| lactose | 150.0 g |
| talc | 21.0 g |
| glycine | 12.5 g |
| stearic acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 3-(3-Ethoxy-4-methoxyphenyl)-N-hydroxy-3-phthalimidopropionamide, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

EXAMPLE 15

Tablets, each containing 10 mg 2-(2,6-dioxo-3-hydroxypiperidin-5-yl)-4-aminoisoindolin-1-one, can be prepared in the following manner:

| Composition (for 1000 tablets) | |
| --- | --- |
| 2-(2,6-dioxo-3-hydroxy piperidin-5-yl)-4-amino isoindolin-1-one | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

EXAMPLE 16

Gelatin dry-filled capsules, each containing 100 mg of 2-(2,6-dioxo-3-hydroxy-5-fluoropiperidin-5-yl)-4-aminoisoindolin-1-one, can be prepared in the following manner:

| Composition (for 1000 capsules) | |
|---|---|
| 2-(2,6-dioxo-3-hydroxy-5-fluoropiperidin-5-yl)-4-aminoisoindolin-1-one | 100.0 g |
| microcrystalline cellulose | 30.0 g |
| sodium lauryl sulfate | 2.0 g |
| magnesium stearate | 8.0 g |

The sodium lauryl sulfate is sieved into the 2-(2,6-dioxo-3-hydroxy-5-fluoropiperidin-5-yl)-4-aminoisoindolin-1-one through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

EXAMPLE 17

A 0.2% injection or infusion solution can be prepared, for example, in the following manner:

| 2-(2,6-dioxo-3-hydroxy piperidin-5-yl)-4-amino-isoindolin-1-one hydrochloride | 5.0 g |
|---|---|
| sodium chloride | 22.5 g |
| phosphate buffer pH 7.4 | 300.0 g |
| demineralized water | to 2500.0 mL |

2-(2,6-Dioxo-3-hydroxypiperidin-5-yl)-4-aminoisoindolin-1-one hydrochloride is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

What is claimed is:

1. A substantially diastereomerically and enantiomerically pure compound selected from the group consisting of (a) an isolindoline of the formula:

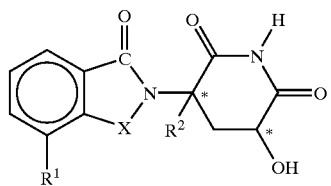

wherein:
the carbon atoms designated * constitute centers of chirality;
X is —C(O)— or —CH$_2$—;
R$^1$ is alkyl of 1 to 8 carbon atoms or —NHR$^3$;
R$^2$ is hydrogen, alkyl of 1 to 8 carbon atoms, or halogeno; and
R$^3$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, benzyl, unsubstituted or substituted with alkyl of 1 to 8 carbon atoms, alkoxy of 1 to 8 carbon atoms, halo, amino, or alkylamino of 1 to 4 carbon atoms, or —COR$^4$ in which R$^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms; and,
(b) the acid addition salts of said isoindoline which are susceptible of protonation.

2. A substantially diastereomerically and enantiomerically pure compound according to claim 1 wherein configuration of the C-3 and the C-5 carbons is (S).

3. A substantially diastereomerically and enantiomerically pure compound according to claim 1 wherein the configuration of the C-3 carbon is (S) and the configuration of the C-5 carbon is (R).

4. A substantially diastereomerically and enantiomerically pure compound according to claim wherein the configuration of the C-3 and the C-5 carbons is (R).

5. A substantially diastereomerically and enantiomerically pure compound according to claim 1 wherein the configuration of the C-3 carbon is (R) and the C-5 carbon is (S).

6. A compound according to claim 1 in which in said isoindoline derivative R$^2$ is hydrogen, methyl, or fluoro.

7. A compound according to claim 2 in which R$^2$ is hydrogen.

8. A compound according to claim 3 in which said isoindoline derivative R$^1$ is amino.

9. A compound according to claim 4 in which said isoindoline derivative X is —C(O)—.

10. A compound according to claim 4 in which said isoindoline derivative X is —CH$_2$—.

11. A compound according to claim 3 in which said isoindoline derivative R$^1$ is methyl.

12. A compound according to claim 2 in which said isoindoline derivative X is —C(O)—.

13. A compound according to claim 2 in which said isoindoline derivative X is —CH$_2$—.

14. The compound according to claim 1 which is 2-(2,6-dioxo-3-hydroxypiperidin-5-yl)-4-aminoisoindoline-1,3-dione.

15. The compound according to claim 1 which is 2-(2,6-dioxo-3-hydroxypiperidin-5-yl)-4-aminoisoindolin-1-one.

16. The compound according to claim 1 which is 2-(2,6-dioxo-3-hydroxypiperidin-5-yl)-4-methylisoindoline-1,3-dione.

17. The compound according to claim 1 which is 2-(2,6-dioxo-3-hydroxypiperidin-5-yl)-4-methylisoindolin-1-one.

18. A method of reducing or inhibiting undesirable levels of TNFα in a mammal which comprises administering thereto an effective amount of a compound according to claim 1.

19. A method of treating in a mammal a disease selected from the group consisting of inflammatory disease, autoimmune disease, arthritis, rheumatoid arthritis, inflammatory bowel disease, Crohn's disease, aphthous ulcers, cachexia, graft versus host disease, asthma, adult respiratory distress syndrome, and acquired immune deficiency syndrome, which comprises administering thereto an effective amount of a compound according to claim 1.

20. A method of treating cancer in a mammal which comprises administering thereto an effective amount of a compound according to claim 1.

21. A method of treating undesirable angiogenesis in a mammal which comprises administering thereto an effective amount of a compound according to claim 1.

22. A pharmaceutical composition comprising (i) a quantity of a compound according to claim 1 that upon administration in a single or multiple dose regimen is pharmaceutically effective and (ii) a pharmaceutically acceptable carrier therefor.

* * * * *